United States Patent
Yan

(10) Patent No.: US 9,556,196 B2
(45) Date of Patent: Jan. 31, 2017

(54) ANTI-PLATELET COMPOUND ADDITION SALT

(75) Inventor: Xiaojing Yan, Beijing (CN)

(73) Assignee: GUANGZHOU HEERSHI PHARMA DEVELOPMENT CO., LTD, Guangzhou (CN)

( * ) Notice: Subject to any disclaimer, the term of this patent is extended or adjusted under 35 U.S.C. 154(b) by 0 days.

(21) Appl. No.: 14/110,898

(22) PCT Filed: Apr. 9, 2012

(86) PCT No.: PCT/CN2012/000468
§ 371 (c)(1),
(2), (4) Date: Oct. 9, 2013

(87) PCT Pub. No.: WO2012/139422
PCT Pub. Date: Oct. 18, 2012

(65) Prior Publication Data
US 2014/0031386 A1    Jan. 30, 2014

(30) Foreign Application Priority Data

Apr. 14, 2011  (CN) .......................... 2011 1 0098528

(51) Int. Cl.
| | |
|---|---|
| *C07D 495/04* | (2006.01) |
| *C07C 309/04* | (2006.01) |
| *C07C 309/19* | (2006.01) |
| *C07C 309/29* | (2006.01) |
| *C07C 309/30* | (2006.01) |

(52) U.S. Cl.
CPC ........... *C07D 495/04* (2013.01); *C07C 309/04* (2013.01); *C07C 309/19* (2013.01); *C07C 309/29* (2013.01); *C07C 309/30* (2013.01)

(58) Field of Classification Search
None
See application file for complete search history.

(56) References Cited

U.S. PATENT DOCUMENTS 6,737,411 B2 *    5/2004   Valeriano et al. .............. 514/39

FOREIGN PATENT DOCUMENTS

| CN | 101591344 A | | 12/2009 |
|---|---|---|---|
| CN | 101675058 A | | 3/2010 |
| CN | 101684124 | * | 3/2010 |
| CN | 101684124 A | | 3/2010 |
| WO | WO2011079407 A | * | 7/2011 |

OTHER PUBLICATIONS

Kozma, Dávid "CRC Handbook of Optical Resolutions via Diastereomeric Salt Formation" 2002 CRC Press: Washington, DC, pp. 52, 66, 93-95, 99, 464-478.*
Stahl "Handbook of Pharmaceutical Salts: Properties Selection and Use" Verlag Helvetica Chimica Acta: 2002, pp. 212-213, 272-273, 294-295, 308-309.*
Stahl and Wermuth, editors, Handbook of Pharmaceutical Salts: Properties, Selection and Use, Weinheim/Zürich:Wiley-VCH/VHCA, 2002.*
Abolghasem Jouyban and Hamed Parsa "Genotoxic Impurities in Pharmaceuticals" in Pharmaceuticals, Toxicity and Drug Testing, Prof. Bill Acree (Ed.), InTech Published Online Feb. 10, 2012, pp. 387-414.*
ICH Harmonised Tripartite Guideline "Stability Testing of New Drug Substances and Products" Current Step 4 version dated Feb. 6, 2003.*
Testa "The Biochemistry of Drug Metabolism—An Introduction Part 5. Metabolism and Bioactivity." Chemistry & Biodiversity—vol. 6 (2009) 626-627.*

* cited by examiner

*Primary Examiner* — David K O Dell
(74) *Attorney, Agent, or Firm* — Locke Lord LLP; Tim Tingkang Xia, Esq.

(57) ABSTRACT

The present invention relates to a use of haloid acid salt and sulfonate of a compound of formula I and a salt of the compound of formula I in preparation of medicament for preventing or treating diseases caused by thrombosis or embolism. The present invention provides acid addition salts, especially haloid acid and sulfonic acid addition salts of a compound of formula I having high inhibition effect on platelet aggregation, and preparation method of the same, a medicament comprising the same, and a use and/or method for preventing or treating diseases caused by thrombosis or embolism.

1 Claim, No Drawings

ANTI-PLATELET COMPOUND ADDITION SALT

TECHNICAL FIELD

The present invention relates to the salts of the novel anti-platelet compound methyl 2-(2-chlorophenyl)-2-(2-acetyl-salicylic acyloxy-4,5,6,7-tetrahydro-thieno[3,2-C]pyridine)-5-acetate (formula I) with good oral absorption and good activity of anti-platelet aggregation, their preparation process, and their use in manufacture of a medicament for treating or preventing thrombus or embolism.

BACKGROUND OF THE INVENTION

China Patent Application No. 200810211286.2 discloses methyl 2-(2-chlorophenyl)-2-(2-acetyl-salicylic acyloxy-4,5,6,7-tetrahydro-thieno[3,2-C]pyridine)-5-acetate (formula I) with good anti-platelet aggregation and its preparation.

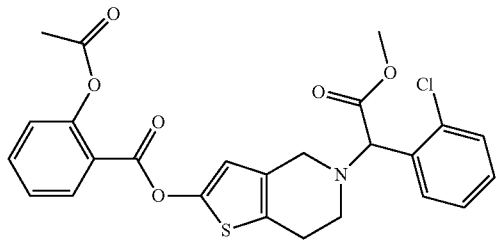

The compound has an excellent inhibitory effect on platelet aggregation and has potential to be an anti-thrombotic agent. However, our studies showed that it has poor water solubility and is unstable in the presence of weak acids and weak bases, easily leading to its degradation products. Thus, the free compound itself is less possible to become a drug. In order to increase the possibility of being a drug, it is necessary to find its suitable derivatives or salts to be used as a active pharmaceutical ingredient (API) with stable physicochemical properties, good absorption and favorable industrial manufacturing process. In addition, the ideal API should possess good oral absorption because anti-platelet medications usually require long-term administration.

SUMMARY OF THE INVENTION

The present inventor has been dedicated to conduct in-depth studies of a variety of pharmacologically active anti-platelet compounds for many years for the purpose of developing good platelet aggregation inhibitors, and finally discovered that certain acid addition salts of the compound of formula I (particularly the salts of hydrohalic acids and the salts of sulfonic acids) are more stable than the corresponding free base compound of formula I and other salts thereof, among which, several salts have excellent oral absorbability and activity of anti-platelet aggregation. In addition, these preferred salts have good stability for storage and handling, and can be used as preventive or therapeutic agents for thrombosis or embolism, thereby forming the present invention.

The present invention provides the acid addition salts of the compound of formula I with excellent anti-platelet aggregation, especially its hydrohalic acid and sulfonic acid addition salts and their preparation methods, the medicament containing them, and the use and/or method for treating or preventing thrombus or embolism.

Thus, in a first aspect, the present invention relates to hydrohalic acid and sulfonic acid addition salts of the compound of formula I.

In a second aspect, the present invention relates to a process for preparing the hydrohalic acid and sulfonic acid addition salts of the compound of formula I.

In a third aspect, the present invention relates to the use of the hydrohalic acid and sulfonic acid addition salts of the compound of formula I in the manufacture of a medicament for treating or preventing thrombus or embolism.

In a fourth aspect, the present invention relates to the method of treating or preventing thrombus or embolism with the hydrohalic acid and sulfonic acid addition salts of the compound of formula I, comprising administering an amount of the hydrohalic acid and sulfonic acid addition salts of the compound of formula I to the subjects in need. Preferably, said subject is a mammal, more preferably a human being.

DETAILED DESCRIPTION OF THE PRESENT INVENTION

The present inventor has discovered that the free compound of formula I is not stable enough in many conditions, such as in the presence of weak acid or base in an aqueous solution for a period of time, producing degradation products. The pure compound of formula I is colorless, and its color deepens gradually after being placed in the air for a long time, first into yellow, then into brick red. Furthermore, the inventor's research indicates that the free compound is of poor water solubility, almost insoluable in water, but soluble in certain organic solvents. It is well-known that a compound to be developed as a drug must have good quality control besides its good safety and efficacy. It is clear that the compound of formula I itself has a low potential to be successfully developed as a drug. Thus, it is necessary to find its suitable API with stable physicochemical properties, good absorption and pharmacological activity in order to increase its potential to be developed as a drug. Additionally, an ideal API should possess good oral absorption as anti-platelet medications usually require long-term administration.

According to the knowledge in chemistry, an acidic or basic compound can form a corresponding basic addition salt or acidic addition salt with higher stability. The compound of formula I is an organic base, and theoretically it can be formed as a salt with organic or inorganic acid to improve its stability.

Surprisingly, the present inventor has discovered that it is very complex for the compound of formula I to form a salt, which is not only related to the types of acids and the purity of the compound of formula I, but also to the conditions forming a salt.

The studies indicate that the compound of formula I cannot form a salt in solid with vast majority of acids, and can only form an oil. However, it can form solid salts with sulfonic acid and hydrohalic acid.

The examples of hydrohalic acids include hydrochloric acid, hydrobromic acid and hydroiodic acid, preferably hydrochloric acid. The examples of sulfonic acids include alkyl and aryl sulfonic acids, among them, alkyl sulfonic acids include methanesulfonic acid, ethanesulfonic acid, propanesulfonic sulfonic acid and camphor sulfonic acid, preferably methanesulfonic acid and camphorsulfonic acid, and aryl sulfonic acids include benzenesulfonic acid, naphthalenesulfonic acid and p-toluenesulfonic acid, preferably benzenesulfonic acid and p-toluenesulfonic acid.

The acid addition salts of the compound of formula I have an asymmetric center in the molecule, including R- and S-stereoisomers, which are encompassed in the present invention, either independently or in any mixed ratio. The S-stereoisomers are preferable, and can be obtained according to a conventional optical resolution, or chromatography, or asymmetric synthesis.

The acid addition salts of the compound of formula I will form hydrates by absorbing moisture while being placed in the air or in the process of recrystallization, thus the acid addition salts containing water are also included in the present invention.

The present invention also relates to the process for preparing the addition salts of the compound of formula I. The process include adding the compound of formula I or its solution in solvent to the hydrogen halide acid, preferably hydrochloric acid, hydrogen chloride (gas), or a sulfonic acid, preferably methanesulfonic acid, benzenesulfonic acid, p-toluenesulfonic acid and camphorsulfonic acid or their solution in solvent Alternatively, the process includes adding or dropping an acid, preferably hydrochloric acid, methanesulfonic acid, benzenesulfonic acid, p-toluenesulfonic acid and camphorsulfonic acid or their solution in solvent to compound of formula I or its solution in solvent once or several times to produce the corresponding salt. Seeds can be added as needed in this method.

With regard to the solvents, as long as they don't affect the reaction and have proper solubility for the compound of formula I, there is no particular limitation. The solvents may be for example, aliphatic hydrocarbons, such as hexane, cyclohexane, heptane, ligroin or petroleum ether; aromatic hydrocarbons such as toluene or xylene; halogenated hydrocarbons such as dichloromethane, chloroform, carbon tetrachloride, 1,2-dichloroethane, chlorobenzene or dichlorobenzene; ether, such as diethyl ether, diisopropyl ether, tetrahydrofuran, dioxane, dimethoxyethane or diethylene glycol dimethyl ether; ester, such as ethyl acetate, methyl acetate, propyl acetate or butyl acetate. In the case of the hydrogen halide salt, preferably ethers, esters, aromatic hydrocarbons, and more preferably diethyl ether, tetrahydrofuran, toluene and ethyl acetate, particularly preferably diethyl ether and toluene, most preferably diethyl ether. In certain embodiments, when the addition salt is a sulfonate, the solvents are preferably ethers, halogenated hydrocarbons, aromatic hydrocarbons, and more preferably tetrahydrofuran, dichloromethane, chloroform, and toluene, most preferably toluene. In certain embodiments, the solvent used is a combination of the above mentioned reagents, or the combination of the above mentioned reagents with an alcohol or/and a ketone reagent. The alcohol includes methanol, ethanol, propanol, isopropanol and butanol, and preferably isopropanol. The ketone includes acetone, methyl ethyl ketone, amyl ketone and cyclohexanone, and preferably acetone.

Although the reaction temperature varies with the reagents or solvents and the like, it is usually −20° C.–100° C., preferably 0° C.-50° C.

Although the reaction time varies with the reagents, solvents or reaction temperature and the like, it is usually 5 minutes to 10 hours, preferably 10 minutes to 5 hours.

After the reaction is complete, the acid addition salts of formula I may be separated from the reaction mixture by conventional methods. For example, after completion of the reaction, the reaction mixture may or may not be kept standing for a certain time, and then the precipitate was filtered. Alternatively, the target compound was obtained by distilling off the solvent after the reaction is complete. The obtained target compound, if necessary, can be further purified by a conventional method, for example, recrystallization, re-precipitation or chromatography.

The acid addition salts of formula I have excellent oral absorption and excellent inhibitory activity of anti-platelet aggregation. In addition, the preferred salts have good storage and handling stability, and can be used as preventive or therapeutic agents for thrombosis or embolism. Moreover, these drugs are preferably used in mammals, and more preferably in human beings.

Industrial Applicability

The acid addition salts of formula I, as preventive or therapeutic agents for thrombosis or embolism, can be mixed with a suitable pharmacologically acceptable excipient, diluents and the like, and administered orally by tablets, capsules, granules, powders or syrups, or non-orally such as injections or suppositories.

These preparations can be manufactured by known methods using the following materials: excipients such as lactose, sucrose, glucose, mannitol, sorbitol and other sugar derivatives, starch derivatives, cellulose derivatives such as crystalline cellulose, gum arabic, dextran, pullulan and other organic excipients; inorganic excipients, such as silicate derivatives, phosphates such as dicalcium phosphate, calcium carbonate, calcium sulfate and the like; lubricants such as stearic acid, calcium stearate, stearic acid metal salts such as magnesium stearate, talc, beeswax, whale wax and other waxes, such as sodium sulfate, glycol, sodium lauryl sulfate, magnesium lauryl sulfate etc.; binders such as hydroxypropyl cellulose, hydroxypropylmethyl cellulose, polyvinyl pyrrolidone, polyethylene glycol and compounds the same as the above excipients; disintegrating agents, such as low-substituted hydroxypropylcellulose, carboxymethyl cellulose, carboxymethyl cellulose calcium and internally cross-linked sodium carboxymethyl cellulose and other cellulose derivatives; stabilizers such as methyl paraben, propyl paraben paraben esters, chlorobutanol, benzyl alcohol, phenylethyl alcohol, benzalkonium chloride, phenols, such as phenol and cresol; flavoring agents such as commonly used sweeteners, acidulants, flavors, diluents, and so on.

The compounds of the present invention may be prepared as formulations for various route of administration, including oral, transdermal, injection, spray or rectally, can be made into tablets, capsules, syrups, powders, granules, emulsions, solutions, suspensions, aerosols and dry powder formulations for systemic or local administration (such as via skin or lung and/or airways).

Although the dosage of drugs varies with the symptoms and age, to an adult, it can be administered orally 1-3 times daily and one dosage is 0.01 mg-1 g/Kg, preferably 0.05 mg-100 mg/Kg, more preferably 0.1 mg-10 mg/Kg, based on compound of formula I.

EXAMPLES

The present invention is further illustrated using S-stereoisomer, which should not be construed as limiting the scope of the present invention. α-bromo-o-chlorophenyl acetate (CAS: 85259-19-4), 5,6,7,7a-tetrahydro-thieno[3,2-c]pyridine-2 (4H)-one or the hydrochloride salt and aspirin and other reagents used in the Example section were obtained commercially.

Example 1

The Process for Preparing the S-Stereoisomer of the Compound of Formula I 337 mg of S(+)-2-(2-chlorophenyl)-2-(4,5,6,7-tetrahydro-thieno[3,2-c]pyridine-2(4H)-one-5-acetic acid methyl ester and 70 mg of sodium hydride (52%, dispersed in mineral oil) were added to a 25 ml reaction flask, and then 2 ml of anhydrous DMF was added. The mixture was stirred for 30 minutes, and then 300 mg of salicylic acid chloride was added and the reaction was continued under stirring for 2 hours. Crude product with 95% purity was obtained after treatment with ethyl acetate. Then 103 mg of the desired product is obtained by chiral preparative chromatography. The yield is 20.6%.

$^1$H-NMR (400 MHz, CDCl$_3$): δ 8.09 (dd, 1H), 7.76-7.80 (m, HI), 7.46-7.53 (m, 2H), 7.32-7.53 (m, 3H), 7.31 (d, 1H), 6.66 (s, 1H), 5.47 (s, 1H), 4.01-4.05 (q, 2H), 3.72 (s, 3H), 3.32-3.40 (broad, 2H), 2.96 (broad, 2H), 2.27 (s, 3H).

ESI-MS: m/z 500.2 (MH$^+$).

Example 2

The 2$^{nd}$ Process for Preparing the S-Stereoisomer of the Compound of Formula I The method was the same as Example 1, except that methyl S(+)-2-(2-chlorophenyl)-2-(4,5,6,7-tetrahydro-thieno[3,2-c]pyridin-2 (4H)-one-5-acetate was replaced with methyl (RS)-2-(2-chlorophenyl)-2-(4,5,6,7-tetrahydro-thieno[3,2-c]pyridine-2 (4H)-one-5-acetate as starting material, with a yield of 21.0%.

Example 3

TABLE 1

Addition salts of the compound of formula I with common acids

| No. | Acid | Physical state of the salt formed | Characteristic of salt | note |
|---|---|---|---|---|
| 1 | Formic acid | oil | — | |
| 2 | Acetic acid | oil | — | |
| 3 | Propionic acid | oil | — | |
| 4 | Butyric acid | oil | — | |
| 5 | Benzoic acid | oil | — | |
| 6 | Parabens | oil | — | |
| 7 | L-mandelic acid | oil | — | |
| 8 | L-tartaric acid | oil | — | |
| 9 | L-camphor sulfonic acid | solid | white solid | |
| 10 | D-camphor sulfonic acid | Sticky solid | — | Oil was formed while base is not pure |
| 11 | methanesulfonic acid | solid | white solid | |
| 12 | Benzeneulfonic acid | solid | white solid | |
| 13 | P-toluenesulfonic acid | solid | white solid | |
| 14 | Maleic acid | oil | — | |
| 15 | Fumaric acid | oil | — | |
| 16 | Oxalic acid | oil | — | |
| 17 | Aspartic acid | oil | — | |
| 18 | Hydrochloric acid | solid | white solid | |
| 19 | Hydrobromic acid | solid | Yellowish solid | |
| 20 | Hydroiodic acid | solid | Yellow solid | |
| 21 | Sulfuric acid | Sticky solid | — | tends to become sticky in the process of salt |
| 22 | Phosphoric acid | oil | — | |

As can be seen from the table, the species of the acids which can form suitable salt with the compound of formula I are very limited and the suitable salts are confined to the hydrohalide and sulfonates.

Example 4

The Preparation of the Addition Salts of S-Isomer of Formula I 4.1 The Preparation of Hydrochloride 500 mg of the compound of formula I was added to a 25 ml reaction flask, and 5 ml of anhydrous ethyl ether was then added. After stirring for 5 minutes, hydrogen chloride in diethyl ether prepared in advance was added dropwise under stirring, and a white precipitate could be observed during the addition. The addition was terminated until no white precipitate emerged and now the pH is about 5. After stirring for another 1 hour, the reaction was stopped, and the reaction mixture was filtered and dried to give 460 mg of a white solid. The yield is 85.8%. TLC: developing system (petroleum ether:ethyl acetate=1:1, with one drop of triethylamine), Rf is 0.4.

$^1$H-NMR (400 MHz, DMSO-d6): δ 8.11 (d, 1H), 7.32-7.81 (m, 7H), 5.40 (broad, 1H), 3.96 (broad, 2H), 3.71 (s, 3H), 3.28 (broad, 2H), 2.94 (broad, 2H), 2.29 (s, 3H).

ESI-MS: m/z 500.2 (MH$^+$).

4.2 The Preparation of Hydrobromide 500 mg of the compound of formula I was added to a 25 ml reaction flask, and 5 ml of anhydrous ethyl ether was then added. After stirring for 5 minutes, hydrobromide in diethyl ether prepared in advance was added dropwise under stirring, and a white precipitate could be observed during the addition. The addition was terminated until no white precipitate emerged and now the pH is about 4. After stirring for another 1 hour, the reaction was stopped, and the reaction mixture was filtered and dried to give 470 mg of a yellowish solid. The yield is 81.0%. TLC: developing system (petroleum ether:ethyl acetate=1:1, with one drop of triethylamine), Rf is 0.4.

4.3 The Preparation of L-Camphor Sulfonate 800 mg of the compound of formula I was added to a 25 ml reaction flask, and 5 ml of toluene was then added. After stirring for 5 minutes, L-camphor sulfonic acid in iso-propanol prepared in advance (370 mg of L-camphor sulfonic acid was dissolved in 0.3 ml iso-propanol) was added dropwise under stirring, and then stirred for another 0.5 hour after addition. After standing in a refrigerator overnight at 4° C. to precipitate a white solid, the mixture is filtered and dried to give 970 mg of a yellowish solid. The yield is 82.9%. TLC: developing system (petroleum ether:ethyl acetate=1:1, with one drop of triethylamine), Rf is 0.4.

$^1$H-NMR (400 MHz, DMSO-d6): δ 8.12 (m, 1H), 7.67 (m, 2H), 7.51-7.54 (m, 3H), 7.36 (d, 1H), 6.71 (s, 1H), 5.49

(broad, 1H), 4.06 (broad, 2H), 3.75 (s, 3H), 3.33 (broad, 2H), 2.98 (broad, 2H), 2.89 (d, 1H), 2.52 (m, 1H), 2.39 (s, 1H), 2.31 (s, 3H), 2.25 (m, 1H), 1.78-1.94 (m, 3H), 1.27-1.29 (m, 2H), 1.03 (m, 3H), 0.74 (m, 3H).

ESI-MS: m/z 500.2 (MH$^+$).

4.4 The Preparation of Methanesulfonate 800 mg of the compound of formula I was added to a 25 ml reaction flask, and 5 ml of toluene was then added. After stirring for 5 minutes, methanesulfonic acid in iso-propanol prepared in advance (160 mg of methanesulfonic acid was dissolved in 0.3 ml iso-propanol) was added dropwise under stirring, and then stirred for another 0.5 hour after addition. After standing in refrigerator overnight at 4° C. to precipitate a white solid, the mixture is filtered and dried to give 750 mg of a yellowish solid. The yield is 78.1%. TLC: developing system (petroleum ether:ethyl acetate=1:1, with one drop of triethylamine), Rf is 0.4.

4.5 The Preparation of Benzenesulfonate 800 mg of the compound of formula I was added to a 25 ml reaction flask, and 5 ml of toluene was then added. After stirring for 5 minutes, benzenesulfonic acid in iso-propanol prepared in advance (260 mg of methanesulfonic acid was dissolved in 0.3 ml iso-propanol) was added dropwise under stirring, and then stirred for another 0.5 hour after addition. After standing in refrigerator overnight at 4° C. to precipitate a white solid, the product is filtered and dried to give 890 mg of a yellowish solid. The yield is 84.0%. TLC: developing system (petroleum ether:ethyl acetate=1:1, with one drop of triethylamine), Rf is 0.4.

4.6 The Preparation of p-Toluenesulfonate 800 mg of the compound of formula I was added to a 25 ml reaction flask, and 5 ml of toluene was then added. After stirring for 5 minutes, p-toluenesulfonic acid in iso-propanol prepared in advance (280 mg of methanesulfonic acid was dissolved in 0.3 ml iso-propanol) was added dropwise under stirring, and then stirred for another 0.5 hour after addition. After standing in refrigerator overnight at 4° C. to precipitate a white solid, the mixture is filtered and dried to give 990 mg of a yellowish solid. The yield is 91.7%. TLC: developing system (petroleum ether:ethyl acetate=1:1, with one drop of triethylamine), Rf is 0.4.

Example 5

The Solubility Test for Several Solid Acid Addition Salt

In general, it is necessary for a drug with good bioavailability to have a good solubility. Typically, the desired solubility of a drug in a pH range of 1-7.5 is at least 1 mg/ml.

TABLE 2

Solubility of Six acid addition salts

| No. | Salt | Solubility (mg/ml) | Note |
|---|---|---|---|
| 1 | L-camphor sulfonate | 4.7 | |
| 2 | Methanesulfonate | 8.2 | |
| 3 | Benzenesulfonate | 2.5 | |
| 4 | P-toluenesulfonate | 1.2 | |
| 5 | Hydrochloride | 0.02 | tends to become sticky in the process of dissolution |
| 6 | Hydrobromide | 0.5 | |

As shown from the table, the four sulfonates of the compound of formula I all have ideal solubility, while the hydrogen halides have relatively worse solubility.

Example 6

Stability Test

A solid active ingredient with excellent stability is necessary for a solid formulation. To screen a suitable salt with chemical stability, the sulfonates prepared above was formulated into tablets or capsules with powdered excipients. The tablets included microcrystalline cellulose and anhydrous calcium dihydrogen phosphate with a ratio of 1:1. The capsules included Mannitol and Corn starch with a ratio of 4:1. And then, the tablets and the capsules were placed at the temperature of 50° C.±2° C. (incubator with constant temperature and humidity) with relative humid of 75% ±5% (saturated sodium chloride solution) for accelerated test. Sampling at the end of the third month, the tablets and the capsules were crushed and extracted with methanol:chloroform (1:1), and TLC was used to check the stability of the product and the salt was deemed as stable with no occurrence of impurity.

TABLE 3

Accelerated stability test for four sulfonates

| No. | Salt | Stability |
|---|---|---|
| 1 | L-camphor sulfonate | Stable |
| 2 | Benzenesulfonate | Stable |
| 3 | P-toluenesulfonate | Stable |
| 4 | Methanesulfonate | Stable |

From the results in the above table, it can be seen that four sulfonates tested were stable; among them, camphor sulfonate is the most stable one.

Example 7

Comparative Efficacy Experiment

To compare the pharmacologic effect between the screened salts and the free compound of formula I, the following arterial thrombosis test was carried out with clopidogrel as the positive drug.

I. Investigation on the Time of Thrombosis Formation,

Animal: wistar rat, 220-260 g in weight, male, 6-8 each group.

Grouping: control group, positive drug group (clopidogrel, 10 mg/kg), free compound of formula I, hydrochloride of the compound of formula I and L-camphor sulfonate of the compound of formula I (two dosages for each group, 3 and 9 mg/kg respectively based on the free compound of formula I).

Method: current injury carotid artery thrombosis method and platelet aggregation test.

Drug Administration: oral gavage.

Index observed: the drug was administrated for consecutive 3 days. 2 hours after the last administration, current injury carotid artery thrombosis method was carried out to observe the time of thrombosis formation. Femoral artery blood was sampled and separated to obtain the platelet. The effect on platelet aggregation was investigated with inducing agent ADP for each group, and at the same time, the bleeding time was determined.

II. Investigation on the Weight of Thrombosis

Animal: wistar rat, 220-260 g in weight, male, 6-8 each group.

Grouping: the same as above.

Method: Arteriovenous shunt thrombosis in polyethylene tube method.

Index Observed The drug was administrated for consecutive 3 days. 2 hours after the last administration, arteriovenous anastomosis thrombosis was lasted for 15 min, the wet weight and dry weight of the thrombosis formed was investigated.

TABLE 4

Anticoagulant effect of the salts of the compound of formula I

| Drug | Dosage (mg/kg) | Thrombosis formation time (s) | Weight of thrombosis (mg) |
|---|---|---|---|
| Control Group | | 88.6 ± 22.2 | 5.4 ± 0.5 |
| Clopidogrel Group | 10 | 249.9 ± 58.0# | 3.2 ± 0.5# |
| Free Base Group | 3 | 165 ± 22.4# | 4.0 ± 0.6# |
| | 9 | 261 ± 54.3#,& | 3.0 ± 0.5#,& |
| Hydrochloride Group | 3 | 210.4 ± 51.1# | 3.2 ± 0.7#,Y |
| | 9 | 319.6 ± 35.2#,H,&,Y | 2.8 ± 0.5# |
| L-camphor sulfonate Group | 3 | 250.4 ± 35.2# ,Y,* | 3.0 ± 0.7#,Y |
| | 9 | 360.2 ± 55.9#,H,&,Y,* | 2.5 ± 0.4#, H,&,Y |

\#: $P < 0.01$, compared with the control group;
H: $P < 0.05$, compared with clopidogrel Group;
&: $P < 0.01$, 9 mg dosage group vs. 3 mg dosage group in each group;
Y: $P < 0.01$, salt vs. oil in same dosage group;
*: $P < 0.01$, L-camphor sulfonate vs. hydrochloride in same dosage The results indicated that anticoagulant effect of the compound of formula I was significantly improved after being formed into a salt in light of the free compound, wherein the sulfonate with stable physicochemical property possessed better efficacy compared with the hydrochloride. The reason might be that low polarity of the compound of formula I leads to poor water solubility, resulting in low oral absorption. Among the stable salts, the sulfonates have better solubility and stability than the hydrochloride, and have higher potential to be developed as a medication.

What is claimed is:

1. A salt, being a sulfonic acid addition salt of a compound of general formula I,

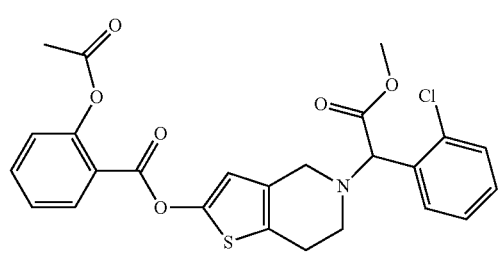

I wherein the compound of general formula I is a S-isomer, and the salt is selected from the group consisting of L-camphorsulfonate and p-toulenesulfonate.

* * * * *